(12) United States Patent
Thielemans et al.

(10) Patent No.: US 7,714,291 B2
(45) Date of Patent: May 11, 2010

(54) METHOD OF AND SOFTWARE FOR CALCULATING A SCATTER ESTIMATE FOR TOMOGRAPHIC SCANNING AND SYSTEM FOR TOMOGRAPHIC SCANNING

(75) Inventors: Kris Filip Johan Jules Thielemans, London (GB); Charalampos Tsoumpas, London (GB)

(73) Assignee: Hammersmith Imanet Limited, London (GB)

( * ) Notice: Subject to any disclaimer, the term of this patent is extended or adjusted under 35 U.S.C. 154(b) by 0 days.

(21) Appl. No.: 11/994,580

(22) PCT Filed: Jul. 7, 2006

(86) PCT No.: PCT/GB2006/002530

§ 371 (c)(1),
(2), (4) Date: Jan. 3, 2008

(87) PCT Pub. No.: WO2007/007063

PCT Pub. Date: Jan. 18, 2007

(65) Prior Publication Data

US 2008/0224050 A1    Sep. 18, 2008

(30) Foreign Application Priority Data

Jul. 7, 2005     (GB) ................................. 0513922.5

(51) Int. Cl.
*G01T 1/161*    (2006.01)
(52) U.S. Cl. ................................. 250/363.03

(58) Field of Classification Search ............ 250/363.03, 250/363.04, 363.07
See application file for complete search history.

(56) References Cited

U.S. PATENT DOCUMENTS

| | | | |
|---|---|---|---|
| 5,390,225 A | 2/1995 | Hawman | |
| 6,490,476 B1 | 12/2002 | Townsend et al. | |
| 6,631,284 B2 * | 10/2003 | Nutt et al. | 600/427 |
| 2002/0036270 A1 * | 3/2002 | Tumer | 250/370.09 |
| 2003/0161521 A1 | 8/2003 | Newport et al. | |

OTHER PUBLICATIONS

Ollinger, J.M., et.al. "Model-based scatter correction for fully 3D PET" Nuclear Science Symposium and Medical Imaging Conference, 1993 IEEE Conference Record, San Francisco, CA, Oct. 31-Nov. 6, 1993 NY, NY Oct. 31, 1993 pp. 1264-1268.

(Continued)

*Primary Examiner*—David P Porta
*Assistant Examiner*—Marcus H Taningco
(74) *Attorney, Agent, or Firm*—Robert F. Chisholm (57) ABSTRACT

The method calculates a scatter estimate for annihilation photons in a subject having a distribution of attenuation. The method can be used for scatter correction of detection data from a positron emission tomographic scanner. The method uses the following steps: —select a first scatter point $S_1$ and a second scatter point $S_2$, —determine a first scatter probability for scattering of a photon at scatter point $S_1$ and a second scatter probability for scattering of a photon at scatter point $S_2$, —determine an integral of the attenuation over a line connecting $S_1$ and $S_2$, —multiply the integral and the scatter probabilities and use the product in the calculation of the scatter estimate.

20 Claims, 5 Drawing Sheets

OTHER PUBLICATIONS

Watson, C.C. "New, faster, image-based scatter correction for 3D PET" Nuclear Science Symposium, 1999. Conference record. 1999 IEEE Oct. 24-30, 1999, Piscataway, NJ, vol. 3, Oct. 24, 1999 pp. 1637-1641.

Ferreira, N.C., et.al., "A hybrid scatter correction for 3D PET based on an estimation of the distribution of unscattered, coincidences: implementation on the ECAT EXAT HR+" Nuclear Science Symposium Conference Record, 2000 IEEE Lyon, France Oct. 15-20, 2000, Piscataway, NJ IEEE, vol. 2, Oct. 15, 2000 pp. 13136-13142.

Wollenweber, S.D. "Parameterization of a model-based 3D PET scatter correction" IEEE Transactions on Nuclear Science, IEEE Service Center, NY, NY, vol. 3, No. 49, Jun. 2002 pp. 722-727.

Accorsi, R, et.al., "Implementation of a single scatter simulation algorithm for 3D PET: application to emission and transmission scanning" 2002 IEEE Nuclear Science Symposium Conference Record/20002 IEEE Nuclear Science Symposium and Medical Imaging Conference, Norfolkk, VA Nov. 10-16, 2002 IEEE Nuclear Science Symposium Conference Record, NY, NY, IEEE, vol. 3 of 3 Nov. 10, 2002 pp. 816-820.

Tsoumpas, C., et.al. "Scatter simulation including double scatter" 2005 IEEE Nuclear Science Symposium Conference Record Oct. 29, 2005.

PCT/GB2006/002530 International search report/written opinion dated Nov. 2006.

GB0513922.5 Search report dated Nov. 2005.

* cited by examiner

METHOD OF AND SOFTWARE FOR CALCULATING A SCATTER ESTIMATE FOR TOMOGRAPHIC SCANNING AND SYSTEM FOR TOMOGRAPHIC SCANNING

This application is a filing under 35 U.S.C. 371 of international application number PCT/GB2006/002530. filed Jul. 7, 2006. which claims priority to application number 0513922.5 filed Jul. 7, 2005 in Great Britain the entire disclosure of which is hereby incorporated by reference.

FIELD OF THE INVENTION

The invention relates to a method for calculating a scatter estimate for annihilation photons in a subject having a distribution of emission and attenuation for scatter correction of detection data from a positron emission tomographic scanner. The invention also relates to software carrying out the method, a data carrier comprising the computer software and a tomographic scanning system adapted for carrying out the method.

BACKGROUND OF THE INVENTION

A typical emission scan using a positron emission tomography (PET) scanner starts with the injection of a solution including a tracer into the subject to be scanned. The subject may be human or animal. The tracer is a pharmaceutical compound including a radioisotope with a relatively short half-life. The tracer has been adapted such that it is attracted to sites within the subject where specific biological or biochemical processes occur. The tracer moves to and is typically taken up in one or more organs of the subject in which these biological and biochemical processes occur.

When the radioisotope decays, it emits a positron, which travels a short distance before annihilating with an electron. The short distance, also called the positron range, is of the order of 1 mm in common subjects. The annihilation produces two high energy photons propagating in substantially opposite directions. The PET scanner includes a photon detector array arranged around a scanning area, usually in a ring-shaped pattern, in which the subject or at least the part of interest of the subject is arranged.

When the detector array detects two photons within a short timing window, a so-called 'coincidence' is recorded. The line connecting the two detectors that received the photons is called the line of response (LOR). The reconstruction of the image is based on the premise that the decayed radioisotope is located somewhere on the LOR. It should be noted that in fact the annihilation occurs on the LOR and the decayed radioisotope is a positron range removed from the point of annihilation. The relatively short positron range may be neglected or can be compensated for in the reconstruction. Each coincidence may be recorded in a list by three entries: two entries representing the two detectors, one entry representing the time of detection. The coincidences in the list can be grouped in one or more sinograms. A sinogram is typically processed using image reconstruction algorithms to obtain volumetric medical images of the subject.

The detector array of a typical PET scanner does not rotate during an acquisition and is generally arranged in two or more banks of stationary detector rings. Alternatively, the detectors may be arranged in a non-ring-shaped pattern. In most detector configurations there will be directions in which coincidences are not detectable due to the geometry of the detector array, since the scanner has a finite field of view and there may be blind spots due to gaps between the detectors.

To obtain quantitative results from a PET scan, the processing must, among others, take into account the attenuation of the photons within the subject. An estimate of the attenuation may be obtained by making test scans in which one or more positron emitter rod sources are arranged in the scanner. The sources may be made of a material such as $^{68}$Ge, which emits dual annihilation photons. Conventionally, two scans are used to derive the attenuation estimate, a blank scan in which the subject being scanned is not present in the scanning area and, typically, the scanner is empty except for the presence of the sources, and a transmission scan in which both the subject and the sources are present in the scanning area. The results of the blank scan are then divided by the results of the transmission scan, providing an attenuation sinogram. The attenuation sinogram can be used to correct the emission scan of the subject for the effects of attenuation.

Another image degrading factor is the scattering of annihilation photons within the subject. Compton scattering is the dominant mechanism of interaction of the photon in the human tissue. The ratio of scattered photons to the total number of photons detected may be up to 50%. The two photons of an annihilation do not in general travel in opposite directions any more after scattering. Hence, the decayed radioisotope will in general not be located on the LOR of a scatter event. Scatter events therefore degrade the image and the detection data are preferably corrected for scatter. A coincidence without scattering resulting from a single annihilation, where the radioisotope lies on the LOR, is called an unscattered event.

A method for scatter correction is known from the article 'New, Faster, Image-Based Scatter Correction for 3D PET' by C. C. Watson in IEEE Transactions on Nuclear Science, Vol. 47, No. 4 (2000) pages 1587-1594. The method reconstructs an image from the detection data that are not corrected for scatter. An estimate of the scatter is calculated using an estimate of the image and of the attenuation. The method calculates a probability for a single-scatter event by tracing two photons resulting from an annihilation, one of which is scattered between the point of annihilation and the detector. The attenuations of the two photons along their paths to the detectors are multiplied with the detector cross sections and the scatter cross-section. A single-scatter estimate is obtained by integrating the probability over all annihilation points and scatter points. A scatter image is reconstructed from the scatter estimate and subtracted from the image derived from the detection data. The resulting image is scatter corrected. An estimate of first and higher order scatter is determined by applying the method for calculating the single-scatter estimate to the non-scatter-corrected image.

A disadvantage of the known method for scatter correction is the inaccuracy of the estimate for the higher-order scatter. It is an object of the invention to provide a method for calculating an improved estimate of higher-order scatter, computer software, a data carrier and a scanner system for carrying out the method.

SUMMARY OF THE INVENTION

The object of the invention is achieved in a method for calculating a scatter estimate for annihilation photons in a subject having a distribution of attenuation for scatter correction of detection data from a positron emission tomographic scanner, using the steps of selecting a first scatter point $S_1$ and a second scatter point $S_2$, determining a first scatter probability for scattering of a photon at scatter point $S_1$ and a second scatter probability for scattering of a photon at scatter point $S_2$, determining an integral of the attenuation over a line connecting $S_1$ and $S_2$, multiplying the integral and the scatter probabilities and using the product in the calculation of the scatter estimate. The method forms the basis of a calculation of an improved estimate of higher-order scatter.

The method is preferably used as part of a method for a scanner having a plurality of detectors around the subject, using the steps of selecting two detectors $D_1$ and $D_2$ from the plurality of detectors, selecting a first scatter point $S_1$ and a second scatter point $S_2$, determining integrals of the attenuation over a first line connecting $D_1$ and $S_1$, a second line connecting $S_1$ and $S_2$ and a third line connecting $S_2$ and $D_2$, determining a first scatter probability for scattering of a photon over a scatter angle equal to an angle between the first and second line and a second scatter probability for scattering of a photon over a scatter angle equal to an angle between the second and third line, and calculating a coincidence probability for detectors $D_1$ and $D_2$ by multiplying the integrals and the scatter probabilities. The word 'line' means a 'straight photon path'. The coincidence rate can be obtained by multiplying with an additional factor for the probability of emission and an integration over the location of the emission. In a particular embodiment the following steps are carried out one or more times: select a further scatter point $S_3$, replace the line connecting $S_1$ and $S_2$ by two further lines connecting the endpoints of the replaced line to the point $S_3$, determine integrals of the attenuation over the two further lines, determine a third scatter probability for scattering of a photon over a scatter angle equal to an angle between the two further lines. If the steps are carried out once, a double scatter estimate is changed to a triple scatter estimate. Each following application of the steps increases the number of scatter events by one. The replacement of one line by two further lines is preferably accompanied by an adaptation of the event at the endpoints of the replaced line, i.e. the scatter angle of a scatter event and/or the detection probability is adapted.

The method can be used for a scatter process wherein the first scatter probability is determined for a higher photon energy than the second scatter probability, the difference in energy being the energy lost in the scatter at point $S_1$. In this process one photon is scattered first at point $S_1$ and next at point $S_2$. The method can also be used for a scatter process wherein the first scatter probability is determined for the same photon energy as the second scatter probability. In this process the annihilation occurs on the line connecting both points and one photon of the annihilation pair is scattered at point $S_1$, the other at point $S_2$.

When integrals are used in the determination of a coincidence probability between detectors of the scanner, the computation time of a scatter simulation can be reduced if the value of the integrals as determined for a first set of detectors and scatter points are cached and used again in the calculation of a coincidence probability for a different, second set of detectors and scatter points. Caching is the storage of information in any form in a retrievable way in any storage means.

A further reduction of the computation time is possible when a method for calculating an estimate for $n^{th}$ order scatter and an estimate for $(n+1)^{th}$ order scatter, where n is an integer equal to or larger than one, includes the steps of caching the value of elements used in the calculation of the estimate for nib order scatter and calculating an estimate for $(n+1)^{th}$ order scatter using the cached values. For example, when carrying out the calculations for the single scatter estimate (n=1), the value of elements can be cached and reused in the calculations for the double scatter estimate (n+1=2). Newly evaluated elements calculated in the latter calculations can also be stored and, together with the elements of the single scatter estimate, used in the calculations for the triple scatter estimate. This embodiment uses the results of the calculation of a lower-order scatter estimate in the calculation of a higher-order scatter estimate. The $n^{th}$ order scatter of a pair of annihilated photons is defined as the process in which the two photons together experience at total of n (Compton) scatter events before being detected. Other forms of scattering, such as Rayleigh scattering, are neglected because of their small probabilities at photon energies which eventually lead to detected events.

In a special embodiment of a method for calculating an estimate for $(n+1)^{th}$ order scatter and an estimate for $n^{th}$ order scatter, where n is an integer equal to or larger than one, includes the steps of caching the value of elements used in the estimate for the $(n+1)^{th}$ order scatter and calculating an estimate for the $n^{th}$ order scatter using the cached values. This embodiment uses the results of the calculation of a higher-order scatter estimate in the calculation of a lower-order scatter estimate.

The elements are preferably integrals of the attenuation, integrals of emission, scatter angles and/or scatter probabilities. When a series of scatter points is the same in the calculation of different order scatters, the line integrals and scatter angles using these points will be the same in the different order scatters. Reuse of cached values of these elements will save computing time.

In a special embodiment of the method the calculation of a coincidence probability is terminated if the energy of a photon after a scatter event is so low that the detection probability of the photon will become negligibly small due to the energy detection window of the detectors. Hence, the calculation of the coincidence probability for such a case can be terminated.

In dynamic PET the attenuation distribution remains constant during a scan but the emission distribution changes. Therefore, in a special embodiment of the method the elements dependent on attenuation and geometry are cached. An example of an element dependent on attenuation is an attenuation integral; an example of an element dependent on geometry is the angle between lines.

In a preferred method the value of elements of the calculation are cached for one value of a parameter and modified to another value of the parameter by multiplication using a scaling factor depending on the parameter. Several elements in the calculation scale with the energy of the photon. An element can then be split in two terms, one independent of the energy and the other term depending only on the energy. Both terms are preferably cached. The calculation of an element can then be reduced to a multiplication of two terms retrieved from memory. The element may be a line integral cached for one value of the photon energy.

In a special embodiment of the method elements of the calculation are cached prior to calculation of the scatter estimate. The prior calculation and storage of the elements reduces the computation time of the scatter simulation, thereby reducing the time between the data acquisition and the availability of the reconstructed image of the subject. The elements are preferably attenuation coefficients and/or detection probabilities. The latter includes two terms; one angle dependent and one angle independent term of the detection probabilities. Elements such as the detection probability and the scatter probability may be cached as a function of photon energy. When the grid of points used in the simulation is known, not only the scatter probabilities but also the scatter angles may be cached before the simulation.

In an advantageous embodiment of a method for calculating a first estimate for $n^{th}$ order scatter and a second estimate for $(n+1)^{th}$ order scatter, where n is an integer equal to or larger than one, the calculation of the first estimate uses more detectors and/or scatter points than the calculation of the second estimate. Since higher order scatter shows less spatial structure than lower order scatter, the calculations for the higher order scatter estimate can be carried out using a reduced number of scatter points and/or detectors. The detectors and scatter points used for the second estimate are preferably a subset of the detectors and scatter points used for the first estimate, thereby allowing the reuse of elements in the calculation based on these detectors and scatter points.

The method for calculating a scatter estimate can advantageously be used in a method of conducting scatter correction for a tomographic scanner including a detector array for detecting radiation for a subject to generate detection data, wherein the method comprises the steps of collecting detection data, calculating the scatter estimate and correcting the detection data for scatter using the scatter estimate. Preferably the method includes the step of determining an image of the subject from the scatter corrected detection data.

In a special embodiment an iterative procedure is used for determining the image of the subject. A step of the procedure may use an estimate up to the $n^{th}$ order scatter, n being equal to one or more, and a subsequent step uses an estimate up to a scatter of order higher than n.

In a preferred embodiment using an iterative procedure for determining the image of the subject, elements used in the calculation of a scatter estimate for a step of the procedure are cached for reuse in a subsequent step. These elements may include integrals. When the iterative procedure updates the estimate of the emission distribution, integrals over the emission need be recomputed, but elements independent of the emission can be cached.

In a special embodiment of the method the first scatter probability and the second scatter probability are dependent and are jointly calculated as a multiple scatter probability. The circumstances where such a joint calculation is advantageous are set out in the detailed description below. When the circumstances apply also to scatter at any further scatter point, such as point $S_3$, the calculation of the scatter probability for this further scatter point is preferably included in the joint calculation with the other scatter probabilities.

A second aspect of the invention relates to computer software for calculating a scatter estimate for annihilation photons in a subject having a distribution of attenuation for scatter correction of detection data from a positron emission tomographic scanner, using a method according to the invention.

A third aspect of the invention relates to a data carrier comprising the above computer software.

A fourth aspect of the invention relates to a tomographic scatter system including a detector array for detecting radiation from a subject to generate detection data, wherein the scatter system is adapted to calculate a scatter estimate for annihilation photons in the subject having a distribution of attenuation for scatter correction of the detection data and using a method according to the invention.

These and other aspects of the invention will be apparent from and elucidated by the way of non-limitative examples with reference to the embodiments described hereinafter and illustrated in the accompanying drawings.

DETAILED DESCRIPTION OF THE INVENTION

Figure 1:
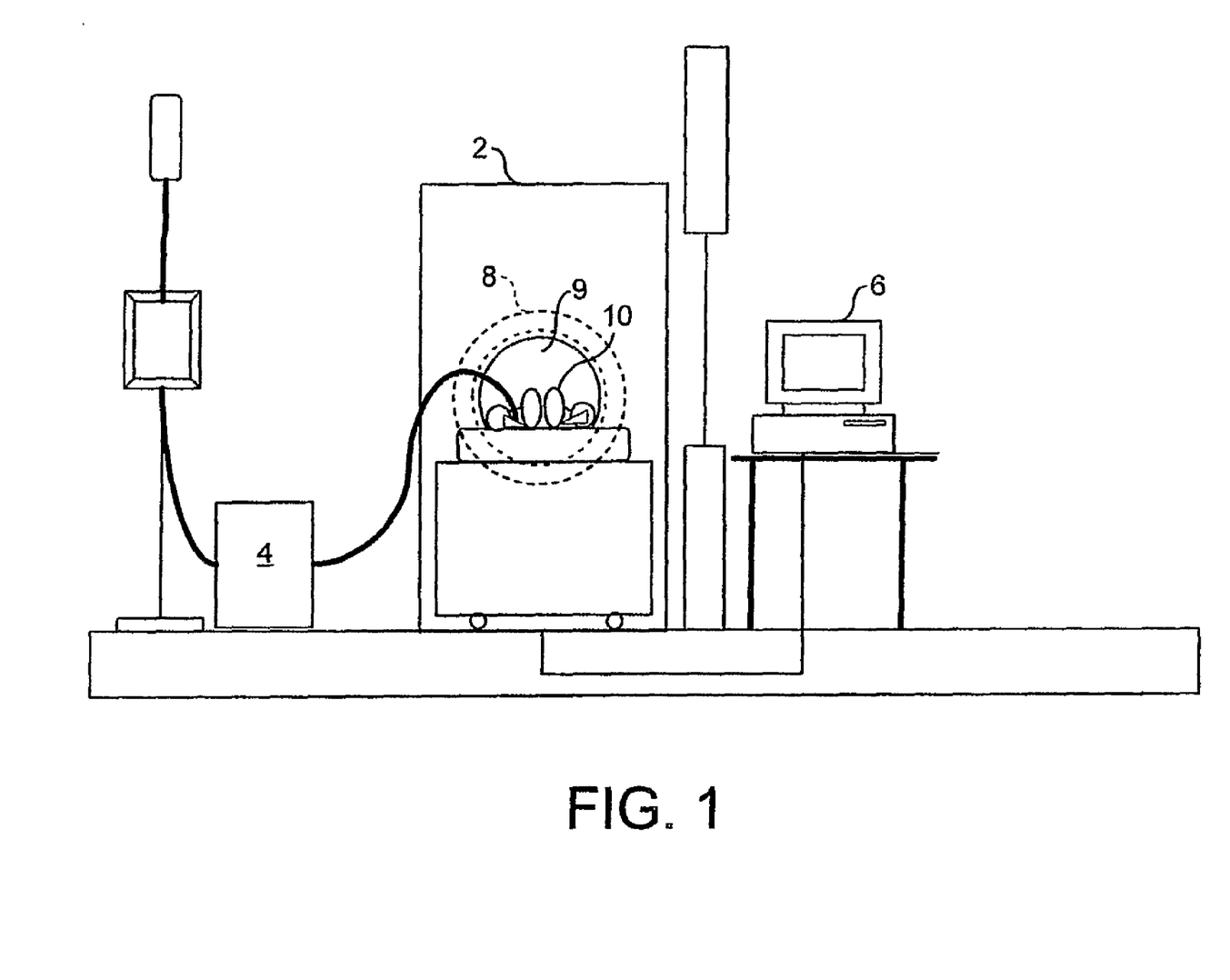
FIG. 1 is a schematic drawing of a PET scanning system.

FIG. 1 shows a tomographic scanner system, arranged in accordance with an embodiment of the invention, which includes a PET scanner 2, a tracer generator module 4 and an operator computer terminal 6. The scanner 2 includes a detector array 8 arranged about a scanning area 9, in which a subject 10 is located during a transmission scan and during an emission scan.

One embodiment of the invention relates to a non-rotating PET scanner, for example, a PET scanner of the ECAT EXACT3D™ type. In this embodiment, the detectors in the detector array 8 are arranged in square detector blocks, each containing multiple detector elements. The detectors blocks are arranged in multiple rings, the rings being arranged adjacent one another along a scanner axis.

Figure 2:
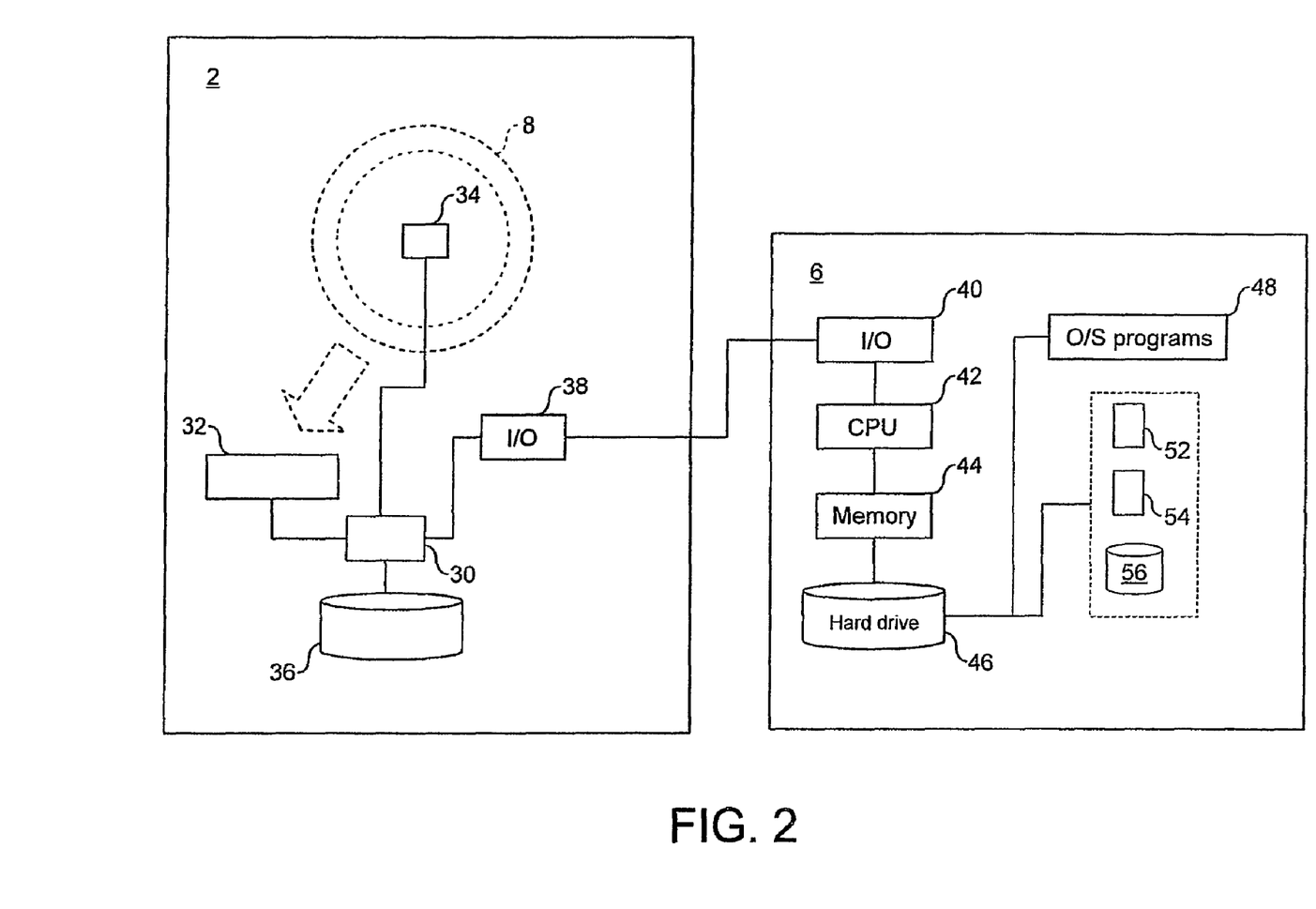
FIG. 2 is schematic drawing of data processing components in a PET scanning system.

As shown in FIG. 2, the PET scanner 2 includes a control unit 30, processing circuitry 32 for detection data received from the detector array, a motion detector 34, a memory 36 for storing the detection data and movement data, and an input/output (I/O) device 38. The computer terminal 6 includes a central processing unit (CPU) 42, a memory 44, a hard disc drive 46 and an I/O device 40, which facilitates interconnection of the computer 6 with the PET scanner 2.

Operating system programs 48 are stored on the hard disc drive 46, and control, in a known manner, low-level operation of the computer terminal 6. Program files and data 50 are also stored on the hard disc drive 46, and control, in a known manner, outputs to an operator via associated devices. The associated devices include a display, a pointing device and keyboard (not shown), which receive input from and output information to the operator via further I/O devices (not shown). Included in the program files 50 stored on the hard disc drive 46 are motion correction software 52 and image reconstruction software 54. A database 56 is used to store the detection data and movement data transferred from the PET scanner 2.

Figure 3:
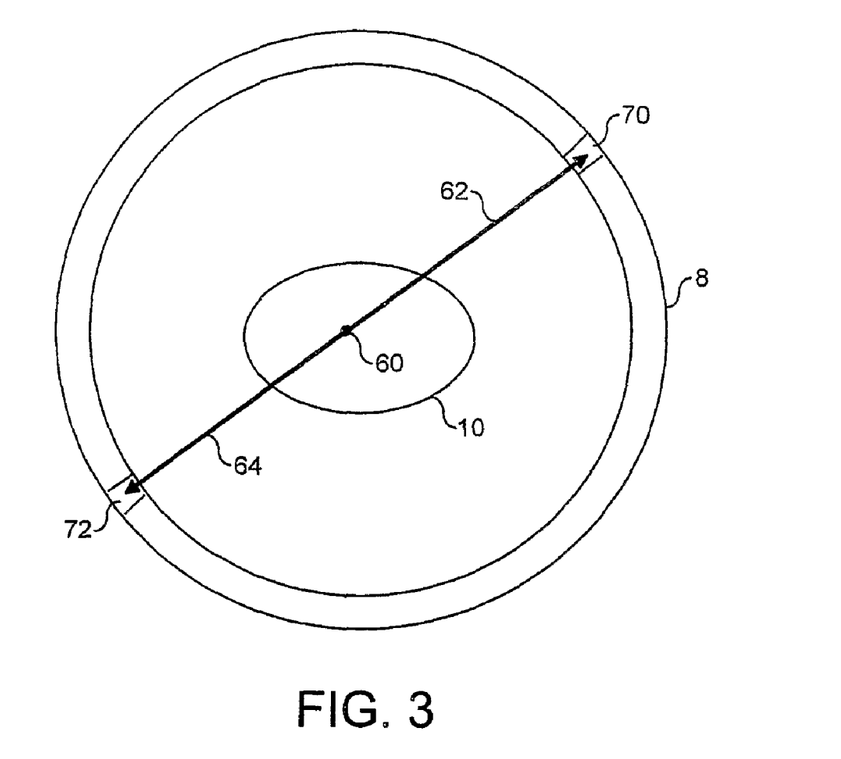
FIG. 3 shows a cross section of a detector array and a subject being scanned.

In acquisition mode, the processing circuitry 32 processes all events detected in the detector array 8 and, by using a coincidence timing window, detects coincidences between the events which are recorded as coincidence counts. These coincidence counts are then output in list-mode to data store 36, where it is stored as a list file for subsequent processing. FIG. 3 illustrates features of operation of the PET scanner during an emission scan. During an emission scan, the subject 10 is placed in the scanning area and contains the tracer generated by the tracer generator module 4. FIG. 3 shows a positron emission event being registered in the detector array 8. The positron 60 annihilates and generates a first photon 62 travelling in one direction and a second photon 64 travelling in the opposite direction. The first photon is detected by a detector element 70 on one side of the detector array 8, and the second photon 64 is detected in a different detector element 72 on the other side of the detector array 8. As described above, the processing circuitry 32 registers the two detection events as a coincidence along a line of response (LOR) defined by the position of the two detector elements 70 and 72.

Figure 4:
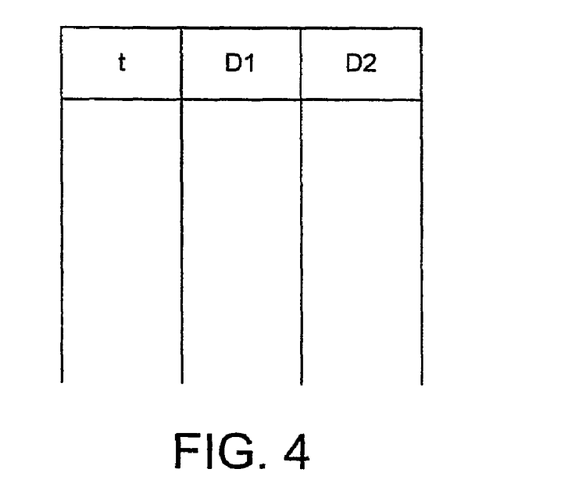
FIG. 4 shows a representation of a list mode file.

FIG. 4 shows a representation of a list file in which the detection data are stored in the memory 36. The file comprises three columns, one for entering the time t of an event and two for entering the detector elements $D_1$ and $D_2$ in which the event was detected. For each coincidence a record is entered in the file, the record comprising the time and two entries identifying the detector elements in which the event was detected. Each set of values $D_1$ and $D_2$ defines a LOR connecting detectors $D_1$ and $D_2$.

Figure 5A:
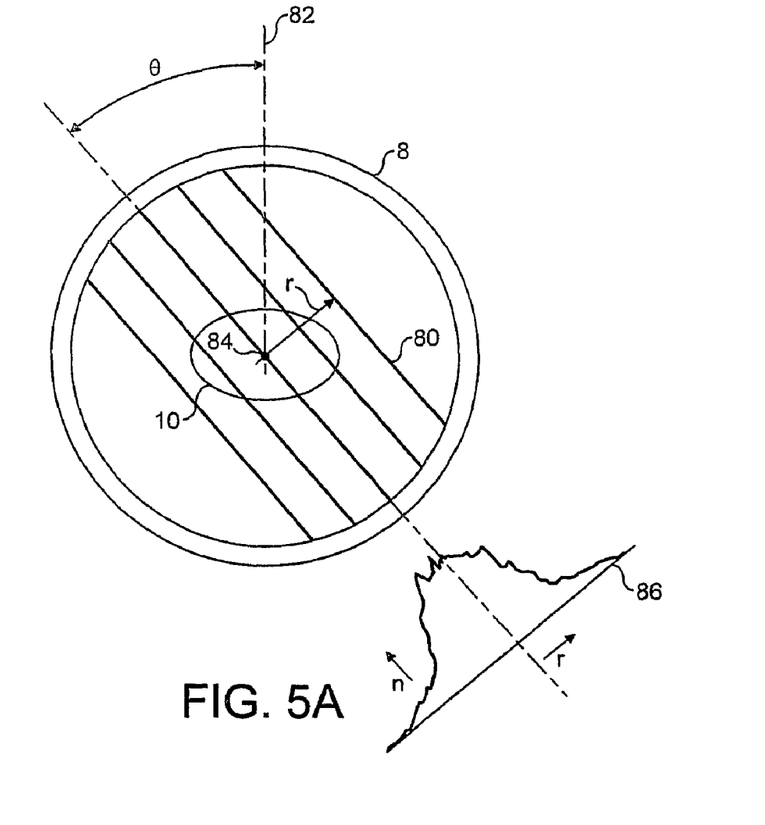
FIG. 5A shows a cross section of the detector array and parameters used in forming a sinogram.
Figure 5B:
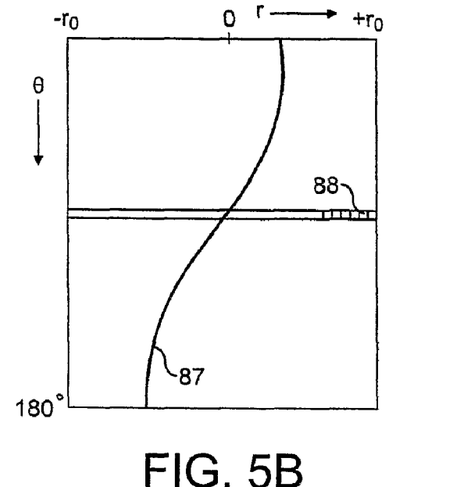
FIG. 5B shows a sinogram.

In some methods of processing detection data the list file is transformed to a sinogram presentation. FIG. 5 shows the parameters used in forming (2-dimensional) sinograms. The transformation starts assigning an angle θ and a distance r to each record in the list file. The angle θ is the angle at which the LOR of the record meets a reference axis 82. The distance r is the shortest distance between the LOR and the centre 84 of the detector array 8. The Figure shows a series of LORs having the same value of the angle θ. Each LOR is stored as a count in a one-dimensional array 86, called a sinogram row. The row comprises a number of bins 88 commensurate with the spatial resolution of the scanner. Each row has assigned to it a specific value of the angle θ and each bin in a row has assigned to it a specific value of the distance r, the distance running from $-r_0$ to $+r_0$, $r_0$ being the distance r pertaining to the first and last bin of the row. The count in a bin is increased by one for each LOR having the values of θ and r pertaining to the bin. The sinogram row is a projection of the radioisotope distribution in a slice of the subject in direction θ. The sinogram rows for all angles θ between 0° and 180° are combined to a sinogram as shown in FIG. 5B. The sinogram derives its name from the fact that an off-centre point source in the subject shows up as a sinusoidal line, for example line 87, in the sinogram.

There are several methods for reconstructing an image of the subject from the detection data. A method based on the point-spread function starts with a test scan using a point source in the scanning area. The detection data of the test scan, in list mode or sinogram mode, form the point-spread function of the scanner. Subsequently, a subject is scanned. The detection data of the subject are deconvolved with the point-spread function, resulting in an image of the subject. Another analytic method uses an inverse Fourier transform. The inverse Fourier transform of a two-dimensional sinogram results in a two-dimensional image of the subject. In iterative methods the quality of the image is improved in a series of repeated steps. It should be noted that in 3D PET scanning the two rings where the protons were detected correspond to two extra coordinates. The text below uses the word 'sinogram' for the whole data-set, in fact a double set of sinograms.

The word 'data' includes among others detection data from the photon detector array and data of the subject relating to position, movement, emission distribution and attenuation.

The image may be degraded by the presence of random events. An example of a random event is an accidental coincidence caused by two annihilations. A random-correction method forms an estimate of the random event rate, for instance by measuring the rate at which two photons are detected in two 10 ns wide windows at a 1 ms delay. Such a delayed detection cannot be caused by photons resulting from a single annihilation. The measured rate can be converted to a zero millisecond delay of the windows, which is the desired random event rate to be used for the correction.

There are several methods to correct the detection data for scattering, disclosed for example in the articles 'Correction for scattered radiation in a ring detector positron camera by integral transformation of the projections' by M. Bergstrom et al in Journal of Computer Assisted Tomography, Vol. 7 (1983) pages 42-50, 'Cross-plane scatter correction-point source deconvolution' by L. Shao and J. S. Karp in PET IEEE Transactions on Medical Imaging, vol. 10(3) (1991) pages 234-239 and 'A convolution-subtraction scatter correction method for 3-D PET' by B. L. Bailey and S. R. Meikle in Phys. Med. Biol., vol. 39 (1994) pages 941-954. In a first scatter-correction method an emitting point source is placed in a scattering medium that is representative for the type of study that will be performed and a test scan is made. The reconstructed image of the point source has a high spatial resolution component and a low spatial resolution background, the latter being due to scatter. This background represents the scatter point spread function of the scanner. The images of the subject are deconvolved with the scatter point spread function, resulting in scatter-corrected images. A similar method can be used directly on sinograms.

The scatter estimate according to the invention is based on a physical model of the scattering process. The model describes the scattering process by a numerical calculation of an integral representing the scatter probability as disclosed e.g. in the article 'Model-based scatter correction for fully 3D PET' by J. M. Ollinger in Phys. Med. Biol. Vol. 41 (1996) pages 153-176. The method starts with an image derived from a reconstruction without motion correction and without scatter correction or with scatter correction based on for example the scatter point spread function. The scatter sinogram of the image is calculated using the physical model and an estimate of the attenuation in the subject. This scatter sinogram is subtracted from the measured sinogram, resulting in a scatter-corrected sinogram. A new image is reconstructed from the scatter-corrected sinogram. The new image can now be used as a second step in an iteration process to calculate again a scatter sinogram. The iteration process results in the scatter-corrected image.

The method of calculating a scatter estimate according to the invention can be introduced in the above method of determining a scatter-corrected image. The physical model includes now a method to determine the single-scatter distribution and the method according to the invention to determine the distribution of double scatter and possibly higher-order scatter.

Figure 6:
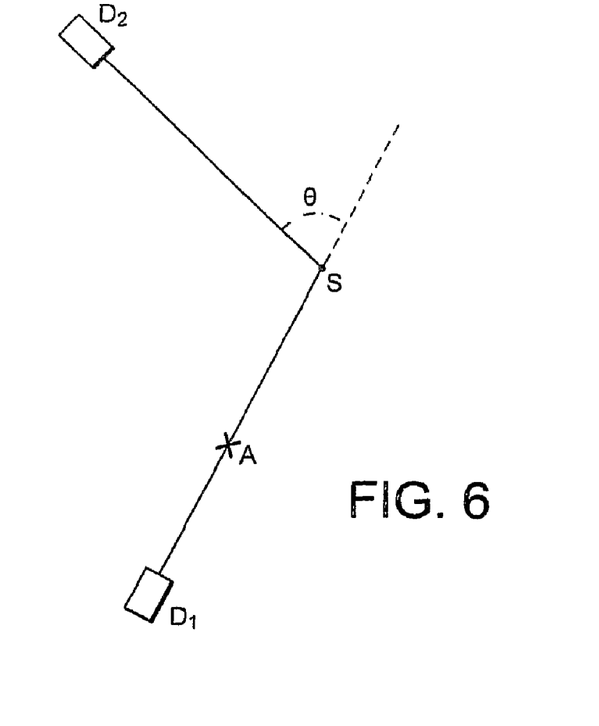
FIG. 6 shows a single scatter event.

The single scatter simulation algorithm will be explained with reference to FIG. 6. The annihilation of a positron occurs at a point A within the subject, from which point two photons are emitted, one towards detector $D_1$ and one towards position S. At scatter point S, the photon is scattered towards detector $D_2$. θ is the scatter angle at S. The single scatter algorithm samples scatter points S in the attenuation image. Then, for each selected scatter point the probability to be scattered and detected by a detector pair is estimated using the Klein-Nishina formula. The sum of the scatter probabilities over all scatter points forms the estimate for the scatter distribution for each detector pair.

Consider two points $d_1$ and $d_2$ on the inner surface of the detector ring of the scanner. The probability density that an electron-positron annihilation at point A results in one photon that scatters at point S and goes towards point $d_1$ and is detected by detector $D_1$, and the other photon goes towards point $d_2$ and is detected by detector $D_2$ is given by:

$$P_{1,0}(A,S,d_1,d_2) = P_{det,D_1}(A \to d_1, E_0) P_{survival}(A \to d_1, E_0)$$
$$P_{emission}(d_1 \leftarrow A \to S) P_{survival}(A \to S, E_0) P_{scat}(S, \theta,$$
$$E_0)) P_{survival}(S \to d_2, E_s(\theta, E_0)) P_{det,D_2}(S \to d_2, E_s(\theta,$$
$$E_0))$$

where:

$$P_{emission}(d_1 \leftarrow A \to S)$$

is the probability density that the photons emitted at point A will go towards $d_1$ and S respectively. Each photon has an energy $E_0=511$ keV immediately after the annihilation. In practice, acollinearity of the two photons emitted at A can be ignored, as its effect is negligible compared to the Compton scatter effect. So, this probability can be modelled by a factor imposing collinearity (i.e. a Dirac delta function) and a factor $1/(4\pi)$ for the probability that the photons are emitted along the line A-S.

$P_{det,X}(Y \rightarrow Z,E)$ is the probability of detection by detector X of a photon of energy E travelling from point Y straight to point Z.

$P_{survival}(X \rightarrow Y,E)$ is the survival probability of a photon of energy E travelling from point X to point Y. In the present case, this is the probability that the photon is not scattered.

$P_{scat}(S,\theta,E)$ is the probability density that a photon of energy E is scattered at point S with scattering angle $\theta$. The angle $\theta$ is fixed by A, S and $d_2$. This can be expressed in terms of the Klein-Nishina formula and the density at point S and, hence, the attenuation image.

$E_s(\theta,E)$ is the energy of a photon scattered over an angle $\theta$ that had energy E before scattering. The energy after scattering is always lower than before, and decreases for larger scatter angle.

A similar probability density $P_{0,1}(A,S,d_1,d_2)$ can be given for the case where the scattered photon is detected by detector $D_2$. The mean number of detected events is determined by multiplying the sum of the probability densities $P_{1,0}(A,S,d_1,d_2)$ and $P_{0,1}(A,S,d_1,d_2)$ with the probability density $P_{annihilation}(A)$ that the annihilation occurred at position A integrating this product over all possible positions of A, S, $d_1$ and $d_2$. This is a 10-dimensional integral (8-dimensional after using the Dirac delta for $P_{emission}(d_1 \leftarrow A \rightarrow S)$) which needs to be computed for all detector pairs. The single-scatter algorithm by Watson does this by introducing several approximations and discretisations. First, the detectors can be considered to be points and only a subset of the total number of detectors in the detector array is considered. The integral reduces to a 4-dimensional integral, i.e. a 3-dimensional integral over the location of the scatter point S and a line integral over the location of the emission point A along the line from the (centre of the) detector $D_1$ to S. The 3 dimensional integral can be computed as a sum over scatter points assumed to lie on a grid. This grid can be relatively coarse grained (voxel sizes of about 2 cm) due to the slow dependence of the Klein-Nishina formula on the scatter angle. It is possible to make a slightly different approximation by taking the finite size of the detectors into account, but keeping the integral over the scatter point similarly discretised, as disclosed by Ollinger.

Computation time may be reduced advantageously by caching various parts of the computation. For instance, the equation for $P_{1,0}$ consists mainly of factors that depend only on the location of the scatter point and a detector. If there are $N_d$ detectors and $N_s$ scatter points, there are $N_d \times N_s$ such factors that can be used for every detector pair and scatter point, i.e. for $N_d \times N_d \times N_s$ computations. These approximations and optimisations make the computation tractable. The computation time for a single-scatter estimate is of the order of a minute on a present-day computer.

Figure 7:
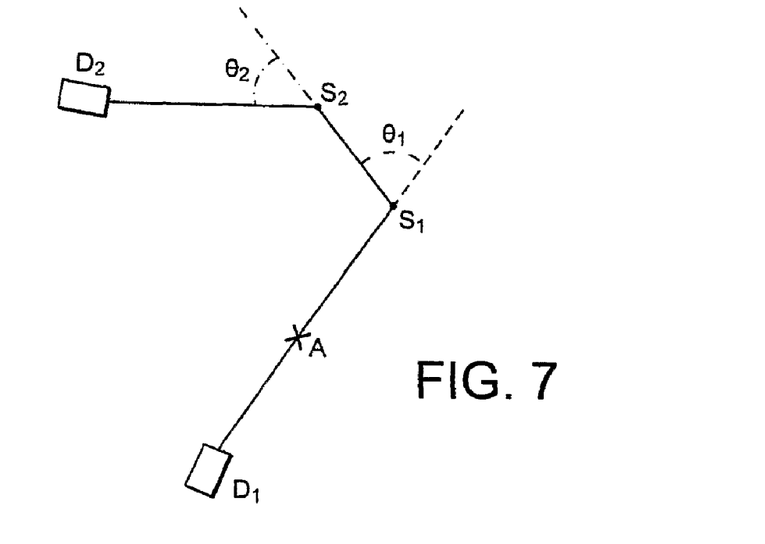
FIG. 7 shows a double scatter event.

The double scatter simulation algorithm according to the invention will be explained with reference to FIG. 7. The annihilation of a positron occurs in position A, from which two photons are emitted, one towards detector $D_1$ and one towards $S_1$. At scatter point $S_1$, the photon is scattered towards point $S_2$. At scatter point $S_2$ the photon scatters for the second time, towards detector $D_2$. $\theta_1$ and $\theta_2$ are the scatter angles of the photon at $S_1$ and $S_2$, respectively. For two points $d_1$ and $d_2$ on the surface of the detector ring of the scanner, the probability density that this annihilation results in one photon that scatters at $S_1$, then at $S_2$ and then goes towards $d_2$ and is detected by $D_2$, and the other photon goes towards $d_1$ and is detected by $D_1$ is:

$$P_{0,2}(A,S_1,S_2,d_1,d_2) = P_{det,D_1}(A \rightarrow d_1, E_0) P_{survival}(A \rightarrow d_1, E_0) P_{emission}(d_1 \leftarrow A \rightarrow S_1) P_{survival}(A \rightarrow S_1, E_0) P_{survival}(S_1 \rightarrow S_2, E_s(\theta, E_0)) P_{2scat}(S_1, \theta_1, S_2, \theta_2, E_0) P_{survival}(S_2 \rightarrow d_2, E_s(\theta_2, E_s(\theta_1, E_0))) P_{det,D_2}(S_2 \rightarrow d_2, E_s(\theta_2, E_s(\theta_1, E_0)))$$

using the notation $P_{0,2}$ to indicate that the photon reaching detector $D_2$ was scattered twice, while the photon reaching detector $D_1$ was not scattered. Here the multiple scatter probability $$P_{2scat}(S_1,\theta_1,S_2,\theta_2,E)$$

is the probability density that a photon of energy E is scattered at point $S_1$ with scattering angle $\theta_1$ and then scattered again at point $S_2$ with scattering angle $\theta_2$, without scatter between $S_1$ and $S_2$. The angle $\theta_1$ is determined by A, $S_1$ and $S_2$, and $\theta_2$ is determined by $S_1$, S2 and d2. This double scatter probability can again be computed in terms of the Klein-Nishina formula and the density at point $S_1$ and $S_2$ and, hence, the attenuation image.

The expression is complicated by the fact that the energy of the photon changes at every scatter. As for the single-scatter case, the scatter angles are fixed by the location of the points. When regarding the detectors as point detectors, the computation of the mean number of detected events requires integration over the location of $S_1$ and $S_2$ and the same line integral (over A) as in the single-scatter case. Several expressions are the same as in the single-scatter case, although at different energy. The term:

$$P_{survival}(S_1 \rightarrow S_2, E_s(\theta,E_0))$$

does not occur in the single-scatter case.

The double scatter case where each photon is scattered only once can be treated in a similar way, resulting in a similar expression, where the emission point A will now be located on the line between $S_1$ and $S_2$. The integration gives rise to a new line integral over the activity distribution between two scatter points.

As will be shown below, the above probabilities for double scatter can be written in terms of some expressions that depend on integrals of the emission and attenuation distributions between two points and other expressions that do not depend on the activity and attenuation distribution but only on the location of the detectors and scatter points. The expressions require the evaluation of integrals between detectors and scatter points, and integrals between two scatter points. The integrals are approximated by summing samples of the integrand at points along the lines.

More explicit expressions for some of the probabilities are given below.

The annihilation probability or emission probability can be expressed as:

$$P_{annihilation}(A) = \lambda(A)$$

with $\lambda(A)$ denoting the concentration of the radio-tracer at point A, ignoring the positron range. When the positron range is taken into account, a marginally blurred version of the concentration distribution will result.

The detection probability $P_{det,X}(Y \rightarrow Z,E)$ generally depends on the energy E of the photon incident on the detector, the energy window used for the acquisition (the upper (ULD) and lower (LLD) limit of discrimination), the detector response probability distribution and the angle φ at which the photon arrives at the detector. The detector response probability distribution represents the probability that a photon having energy E deposits an energy $E_f$ in the detector. The deposited energy must fall between the upper and lower limit of discrimination to detect the photon. The detector response probability distribution is normally modelled using a Gaussian distribution to take the finite energy resolution of the detectors into account. The mean value of the Gaussian distribution is E and its standard deviation (σ) is dependent on the response of the detector. Often the standard deviation is modelled as proportional to the square root of the energy of the photon E. Most present scanners use an energy window. If the detected energy is outside this window, the event is rejected. The detection probability $P_{det,X}(Y \to Z, E)$ can thus be modelled as an integral of the above Gaussian distribution over the energy window times a factor depending on the incidence angle φ. In a simple model the angle dependence of the detection probability is expressed as cos(φ).

The survival probability can be expressed as:

$$P_{survival}(X \to Y, E) = \exp\left(-\int_0^1 \mu(lX + (1-l)Y; E)\,dl\right)$$

with μ(B;E) the attenuation coefficient at energy E at point B. This is Beer's law. When the attenuation coefficient μ(B; E) is written as μ(B;E)=μ(B;E₀)f(E), that is, the attenuation coefficient at a given energy is proportional to the attenuation coefficient at 511 keV, then:

$$P_{survival}(X \to Y, E) = \exp\left(-f(E)\int_0^1 \mu(lX + (1-l)Y; E_0)\,dl\right)$$

When the value of the line integral between X and Y of the attenuation distribution at 511 keV is known, the survival probability over the same line for a photon having a different energy can be determined using the multiplication of the known integral value with an energy-dependent factor and exponentiation.

The probability for detecting a single scatter event can be rewritten in terms of the above result (re-ordering the factors of the equation), as the integral over S of the following expression:

∫dAdd₁dd₂P₁,₀(A,S,d₁,d₂)=1/(4π)∫dd₁dd₂L(d₁,S)exp
[−M(d₁,S)]P_{det,D1}(S→d₁,E₀)P_{scat}(S,θ,E₀)exp
[−f(E_s(θ,E₀))M(S,d₂)]P_{det,D2}(S→d₂,E_s(θ,E₀))

where the integral over A is a line integral over the activity and where:

$$L(X, Y) = \left(\int_0^1 dl\, \lambda(lX + (1-l)Y)\right);$$

and $$M(X, Y) = \left(\int_0^1 dl\, \mu(lX + (1-l)Y; E_0)\right)$$

The above expression for the single scatter probability can be approximated by taking into account that the detection probabilities are negligible unless the points $d_i$ are close to the corresponding detector $D_i$. The scatter angle can thus be taken as constant over the non-zero range of the integrand. This means that the integral can be separated into two separate integrals:

∫dAdd₁dd₂P₁,₀(A,S,d₁,d₂)=1/(4π)P_{scat}(S,θ,E₀)[∫dd₁L
(d₁,S)exp [−M(d₁,S)]P_{det,D1}(S→d₁,E₀)][∫dd₂ exp
[−f(E_s(θ,E₀))M(S,d₂)]P_{det,D2}(S→d₂,E_s(θ,E₀))]

These two integrals depend only on the location of the scatter point and the detector and (for the second integral) the scatter angle. So they can be cached and reused for other detector pairs. This is particularly effective if in the second integral the dependence of M(S,d₂) on d₂ is small. In that case this integral can be approximated by:

exp [−f(E_s(θ,E₀))M(S,c₂)]∫dd₂P_{det,D2}(S→d₂,E_s(θ,E₀)), where the line integral through the attenuation is computed for a central point c₂ on the inner surface of the detector. This approximation can be improved by linearising the exponential around M(S,c₂), i.e.:

exp [−f(E_s(θ,E₀))M(S,d₂)]≈[1+f(E_s(θ,E₀))(M(S,c₂)−M
(S,d₂))] exp [−f(E_s(θ,E₀))M(S,c₂)]

To summarise, the single scatter estimate can be approximated by integrals that do not depend on the scatter angle, and consequently the computation time increases only linearly with the number of detectors and scatter points.

The probability for detecting a double scatter event for the case one annihilation photon is scattered at $S_1$ and $S_2$ can be written as:

∫dAdd₁dd₂P₀,₂(A,S₁,S₂,d₁,d₂)=1/(4π)∫dd₁dd₂L(d₁,S₁)
exp [−M(d₁,S₁)]P_{det,D1}(S₁→d₁,E₀)P_{2scat}(S₁,θ₁,S₂,
θ₂,E₀)exp [−f(E_s(θ₁,E₀))M(S₁,S₂)]exp [−f(E_s(θ₂,
E_s(θ₁,E₀)))M(S₂,d₂)]P_{det,D2}(S₂→d₂,E_s(θ₂,E_s(θ₁,
E₀)))

The integrated double scatter probability for this case is an integral over all possible positions of $S_1$ and $S_2$ of the above expression. The double scatter probability for the case each annihilation photon scatters once before detection is:

∫dAdd₁dd₂P₁,₁(A,S₁,S₂,d₁,d₂)=1/(4π)∫dd₁dd₂ exp [−f
(E_s(θ₁,E₀))M(d₁,S₁)]P_{det,D1}(S₁→d₁,E_s(θ₁,E₀))
P_{11scat}(S₁,θ₁,S₂,θ₂,E₀)L(S₁,S₂)exp [−M(S₁,S₂)]
exp [−f(E_s(θ₂,E₀))M(S₂,d₂)]P_{det,D2}(S₂→d₂,E_s(θ₂,
E₀))

with $P_{11scat}(S_1,θ_1,S_2,θ_2, E_0)$ the probability density that both annihilation photons (of energy $E_0$) are scattered, one at point $S_1$ with scattering angle $θ_1$ and the other at point $S_2$ with scattering angle $θ_2$ (given that they do not scatter between $S_1$ and $S_2$). This double scatter probability can be computed using quantum mechanics and the Klein-Nishina formula and the density at point $S_1$ and $S_2$ and, hence, the attenuation image.

The single scatter probability $P_{scatt}$ can be written as:

$$P_{scatt}(S, θ, E) = \frac{\mu(E, S)}{\sigma(E)} \frac{d\sigma(θ, E)}{d\Omega},$$

where dσ/dΩ is the probability density for Compton scattering, given by:

$$\frac{d\sigma}{d\Omega} = \frac{r_o^2}{2}\left(1 + \frac{a^2(1-\cos θ)^2}{(1+\cos^2 θ)[1+a(1-\cos θ)]}\right)\frac{1+\cos^2 θ}{[1+a(1-\cos θ)]^2}$$

where $r_0$ is the classical electron radius, $2.818 \, 10^{-15}$ m, a is the energy E of the photon normalized to 511 keV, and $\sigma(E)$ is the total cross section, obtained by multiplying the scatter probability density by $2\pi \sin \theta$ and integrating over $\theta$.

The multiple scatter probability for higher-order scatter can be computed from the above scatter probability using quantum mechanics. A complication is that photons have a quantum number corresponding to polarization. Although this polarization is not detected in current scanners, one should use the polarized Klein-Nishina equation during the calculation, and then average over the possible polarization angles. In addition, the two annihilation photons are not independent, as their polarization vectors have to be orthogonal and the photons are entangled. A correct quantum-mechanical derivation of the normalized scatter probability density for the case where each photon scatters once is given in Snyder H S, Pastemack S and Hornhostel J 1948 Phys. Rev. 73 440-448 with the following result:

$$\frac{d^2\sigma}{d\Omega_1 d\Omega_2} = \frac{k_1^2 k_2^2 \begin{pmatrix} \gamma_1 \gamma_2 - \gamma_1 \sin^2\theta_2 - \gamma_2 \sin^2\theta_1 + \\ 2\sin^2\theta_1 \sin^2\theta_2 \sin^2\omega \end{pmatrix}}{4\pi^2 k_0^4 \left(\frac{40}{9} - 3\ln 3\right)^2} \text{ where}$$

$$\gamma_1 = \frac{k_1}{k_0} + \frac{k_0}{k_1}, \gamma_2 = \frac{k_2}{k_0} + \frac{k_0}{k_2}.$$

In this equation $d\Omega_1$ and $d\Omega_2$ are the differential solid angles for the scattered photons, $k_1$ and $k_2$ are their momentum magnitudes (proportional to their energy), $\theta_1$ and $\theta_2$ are their scattering angles and $\omega$ is the angle between the two planes of scattering. However, if the scattering angle for both annihilation photons is less than about 30 degrees, then there is little variation with the angle $\omega$ and effectively the entanglement can be ignored as the probability distribution is approximately the same as the product of two unpolarized single scatter distributions. In most cases, the photons with larger scatter angle will not be detected due to the energy windowing. In these circumstances the probability that both photons scatter once can in good approximation be written as a product of two single scatter probabilities:

$$P_{1\text{scatt}}(S_1,\theta_1,S_2,\theta_2,E_0) \approx P_{\text{scatt}}(S_1,\theta_1,E_0)P_{\text{scatt}}(S_2,\theta_2,E_0)/|S_1-S_2|^2$$

with the denominator being the distance between the two scatter points, due to a geometric effect.

For the case where one photon scatters twice, a derivation of the scatter probability is given in A. Wightman 1948 Phys. Rev. 74 1813-1817. Again, if low energy photons are not detected, in good approximation $$P_{2\text{scatt}}(S_1,\theta_1,S_2,\theta_2,E) \approx P_{\text{scatt}}(S_1,\theta_1,E)P_{\text{scatt}}(S_2,\theta_2,E_s(\theta_1,E))/|S_1-S_2|^2$$

Wightman also gives general expressions that can be used to compute higher order scatter probabilities.

Hence, when the scattering angles are larger than about 30 degrees, the scatter probabilities are dependent and the above approximations are less good; in such circumstances the scatter probabilities are preferably jointly calculated as a multiple scatter probability.

The first step in making the scatter estimation computation feasible is to use approximations, in particular the approximation that the scatter angles can be kept constant during the above integrations and that the energy dependence of the survival probabilities can be factored out. This means that the double scatter probability can be computed in terms of integrals which depend only on two scatter points or on a detector and one scatter point. Since the computation of the integrals is time-consuming, their values are preferably cached, thereby allowing reuse of the values. The end points of the line of integration are preferably on the same grid as the points where the emission and attenuation have been determined. More preferably, the end points and the points where the integrand are sampled are on the same grid. Integrals of the single-scatter simulation can be used in the double-scatter simulation when the points of the grid of the double-scatter simulation correspond to points of the grid of the single-scatter simulation. For instance, when the point S in FIG. 6 is at the same location as point $S_1$ in FIG. 7, the values of the integrals from the detector $D_1$ to S calculated in the single-scatter simulation can be reused in the double-scatter simulation. Hence, the line integrals of the single-scatter simulation are preferably stored, not only for the computation of the single-scatter simulation itself, but also for the calculation of the double-scatter simulation and higher-order scatter simulation. Similarly, the line integrals computed for the double-scatter simulation are preferably cached to allow reuse of their values. For example, the emission and attenuation integrals over the line $D_1$ to $S_1$ in FIG. 7 can be used for any probability P where $D_1$ and $S_1$ are at the same position but $S_2$ and $D_2$ are at positions different from those in FIG. 7. Similarly, terms in the probability equation that depend on the scatter angle only should be cached for reuse in the simulation itself and any higher-order scatter simulation.

The final integrals over $S_1$ and $S_2$ can for instance be computed by choosing the scatter points on a grid and summing the contributions for all pairs of points. Alternatively, more sophisticated numerical methods for computing this 6-dimensional integral can be used, for instance using sparse grids as disclosed in the article "High dimensional integration of smooth functions over cubes" by E. Novak and K. Ritter, Numer. Math. Vol. 75 (1996) pages 79-97.

The number of points in the grid used for determining the double-scatter simulation may be fewer than the number of points in the grid of the single-scatter simulation because the distribution of higher-order scatter shows less spatial detail than the distribution of lower-order scatter. The above relations between the single- and double-scatter simulation for reuse and spatial detail apply generally between $n^{th}$ order and $(n+1)^{th}$ order scatter simulation, where n is equal to or larger than one.

The computation time can be reduced by preparing tables containing intermediate results before starting the simulation. The attenuation coefficient at energy E and position B can be written as a product of an energy-dependent term f(E) and an attenuation $\mu(B;E_0)$ at energy $E_0$. A table of f(E) as a function of E can be made before the simulation. Similarly, a second table of $\mu(M;E_0)$ for various materials M can be made before the simulation. The materials may relate to the subject, e.g. water, blood, bone, brain, heart, and to the surroundings of the subject, e.g. iron, lead, NaI, tungsten, PMMA. When during the simulation a value of the attenuation coefficient at a position B is required, the value of f(E) is taken from or interpolated in the first table, the value of $\mu$ is taken from the second table in dependence on the material M present at position B, and both values are multiplied. In a different setup, a table of values $\mu(M;E)$ is provided for each material M used in the simulation, in which the attenuation is given as a function of E.

Values for the detection probability $P_{det,X}$ for a photon incident on detector X can also be stored before the calculation of the photon paths. As discussed above, the detection probability can be expressed as a product of a function $P_0(E)$ of the photon energy (E) and a function $f(\phi)$ of the incidence angle ($\phi$). Due to the energy window, $P_0(E)$ will be very small for low photon energies. In practice the calculation of the photon path is terminated when the photon energy is less than a threshold, also called the scatter energy threshold. For instance, for the Gaussian model, this threshold can be taken to be LLD-2$\sigma$. The values of the thresholds and the detector response probability distribution are generally fixed values and are usually proposed by the manufacturer as being optimal for simulation of a scan. The value of $P_0(E)$ as function of E can be stored in a table before the simulation. The values of $P_0$ are the same for all detectors, apart from a possible detector-dependent calibration constant. The calculation of a detection probability during the simulation requires retrieving a value of $P_0$ from the table in dependence on the energy of the photon, multiplying this value with $f(\phi)$ and, if required, multiplying with the calibration constant. The value of $f(\phi)$ may be stored in a table as a function of the angle $\phi$ before the calculation of the photon paths or during the simulation.

The scatter angles $\theta_1$ and $\theta_2$ in the scatter probability formulas require the calculation of the angle between two lines. The calculated angles can also be stored as a function of the parameters of the lines during the simulation, preferably as a function of the direction vectors of the lines. When the highest-order scatter estimate used in the simulation is calculated before the lower-order scatter estimates, the lower-order scatter estimates do not require calculation of angles anymore, because all angles can be taken from the table. When the grid of annihilation points and scatter points and preferably the detection points is the same for all scatter measurements, the angles can also be stored before carrying out the simulation, which has the advantage that no angles between lines have to be calculated during the simulation.

The values of the attenuation p and the (total) cross section for Compton scattering a can be derived from tables. The values of the scatter probabilities can be calculated before the scatter simulation if fixed scatter points are used during the simulation and then stored in a table as a function of energy or entered in the table when calculated during the simulation. The range of energies should be commensurate with the lower limit of discrimination of the detectors.

The computation time can also be reduced by preparing a table of values of the cross-section $\sigma(E)$ as a function of the energy E. Since the cross-section does not depend on the material, only a single table suffices. The table can be prepared before the simulation.

The total scatter estimate for first to $n^{th}$ order scatter estimates can be calculated by starting the calculation of the $n^{th}$ order scatter estimate and subsequently calculating the next lower order scatter estimate. After the calculation of the $n^{th}$ order scatter estimate all parameters for the lower order scatter estimates are in the tables. The lower order scatter estimates can now be calculated by mainly multiplying and raising to a power the values taken from the tables in order to obtain the probabilities for one photon path and adding the probabilities for all possible photon paths. In case more scatter points are used for lower order scatter, this scheme has to be modified to extend the tables accordingly.

The computational effort for double and higher-order scatter simulation may be reduced firstly by the above mentioned use of caching and reusing earlier computed values. Secondly, it may be reduced by the mentioned decrease in spatial detail for higher-order scatter, which allows more approximations to be made in the calculation, such as reduction of the number of scatter points and/or detectors. Thirdly, the contribution of higher-order scatter to the total scatter distribution decreases rapidly. Since each scatter decreases the energy of the photon, the probability increases that a multiply scattered photon falls below the lower energy threshold. These reductions make multiple scatter simulation using present-day computers feasible. For example, a simulation taking single and double scatters into account takes approximately ten minutes for a 3D PET acquisition.

In the iterative approach, the computational effort can also be reduced. First, since the attenuation image does not change over iterations, the scatter points may be selected once during the first iteration and maintained for subsequent iterations. Hence, the line integrals through the attenuation image need to be computed only once. Second, at the start of the process, the input data is usually contaminated by abundant scatter, hence the first and possibly several more iterations may use a relatively crude scatter simulation method. A possible scheme may be to use the single scatter simulation with rescaling in the first iteration(s), and include second and possibly higher order scatter simulation for subsequent iterations. In addition, the number of scatter points and/or detectors may be taken very small at the start and increased at a later stage.

In some cases the physical model of the scattering process does not provide a sufficiently accurate quantitative estimate of the scatter, e.g. because of scatter from parts of the body outside the field of view of the scatter. The accuracy of the estimate can be improved by scaling the estimate. Scaling is carried out by multiplying the counts in the scatter estimate by one or more scaling factors. A fit of the scatter estimate to the detection data provides a value of the scaling factor. In the so-called tail fitting method the fit is performed only on those LORs in a list or sinogram that do not intercept the subject and which therefore relate to scatter events.

The method according to the invention provides a good estimation of the scattered events in cases where the complete activity and attenuation distribution are known. When the distribution is not well known, such as in the case of Out of Field Of View (FOV) scatter, various approaches may be used to obtain a good estimate. The following four approaches are by way of example only and do not exclude other approaches. In the first place short acquisition of neighbouring regions may be used, e.g. using bed movement. The acquisition may be short because the quality of the data need not be very high to obtain reasonable scatter estimates. In the second place use of modelling of the neighbouring regions can be feasible based on population data. For instance, the liver might be modelled as a uniform region in case of tracers with high uptake; hence, it can be taken into account even if only a part of the liver is imaged. In the third place, hybrid scatter methods may be used, such as disclosed in the article 'A Hybrid Scatter Correction for 3B PET' by N.C. Ferreira et al in Phys. Med. Biol. (2002) pages 1555-1573, but then combined with a more accurate method than single-scatter simulation. In the fourth place, scatter tail fitting can be used as in the article 'A single-scatter simulation technique for scatter correction in 3D PET' by C.C. Watson et al in the book 'Three-dimensional Image Reconstruction in Radiation and Nuclear Medicine' Kluwer, 1996, ISBN 0 7923 4129 5) pages 255-268.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for calculating a scatter estimate for annihilation photons in a subject having a distribution of attenuation for scatter correction of detection data from a positron emission tomographic scanner, using the following steps:
   selecting a first scatter point $S_1$ and a second scatter point $S_2$ for the detection data for the subject from the positron emission tomographic scanner,
   determining a first scatter probability for scattering of a photon at scatter point $S_1$ and a second scatter probability for scattering of a photon at scatter point $S_2$,
   determining an integral of the attenuation over a line connecting $S_1$ and $S_2$,
   multiplying the integral and the scatter probabilities and using the product in the calculation of the scatter estimate.

2. A method according to claim 1, wherein the first scatter probability is determined for a higher photon energy than the second scatter probability, the difference in energy being the energy lost in the scatter at point $S_1$.

3. A method according to claim 1, wherein the first scatter probability is determined for the same photon energy as the second scatter probability.

4. A method according to claim 1 in which the line integral is used in the determination of a coincidence probability between detectors of the scanner, including the steps:
   cacheing the value of the integral as determined for a first set of detectors and scatter points and
   use the value in the calculation of a coincidence probability for a different, second set of detectors and scatter points.

5. A method for calculating an estimate for $n^{th}$ order scatter and an estimate for $(n+1)^{th}$ order scatter, where n is an integer equal to or larger than one, including the steps:
   cacheing the value of elements used in the calculation of the estimate for $n^{th}$ order scatter and
   calculating an estimate for $(n+1)^{th}$ order scatter according to claim 1, using the cached elements.

6. A method for calculating an estimate for $(n+1)^{th}$ order scatter and an estimate for $n^{th}$ order scatter, where n is an integer equal to or larger than one, including the steps:
   cacheing the value of elements used in the estimate for the $(n+1)^{th}$ order scatter calculated according to claim 1 and
   calculating an estimate for the $n^{th}$ order scatter using the cached elements.

7. A method according to claim 5, wherein the elements are integrals of the attenuation, integrals of emission, scatter angles and/or scatter probabilities.

8. A method according to claim 1, wherein the calculation of a coincidence probability is terminated if the energy of a photon after a scatter event is lower than a predetermined threshold value.

9. A method according to claim 1, wherein the value of elements of the calculation are cached for one value of a parameter and modified to another value of the parameter by multiplication using a scaling factor depending on the parameter.

10. A method according to claim 9, wherein the elements are integrals cached for one value of the photon energy.

11. A method according to claim 1, wherein elements of the calculation are cached prior to calculation of the scatter estimate.

12. A method according to claim 11, wherein the elements are attenuation coefficients, detection probabilities, scatter probabilities, and/or scatter angles.

13. A method according to claim 12, wherein the elements are cached as a function of energy.

14. A method for calculating a first estimate for $n^{th}$ order scatter and a second estimate for $(n+1)^{th}$ order scatter, where n is an integer equal to or larger than one and the estimate for $(n+1)^{th}$ order scatter is calculated according to claim 1, wherein the calculation of the first estimate uses more detectors and/or scatter points than the calculation of the second estimate.

15. A method of conducting scatter correction for a tomographic scanner including a detector array for detecting radiation for a subject to generate detection data, wherein the method comprises the steps:
   collecting detection data
   calculating a scatter estimate according to claim 1
   correcting the detection data for scatter using the scatter estimate.

16. A method according to claim 15, including the step of determining an image of the subject from the scatter corrected detection data.

17. A method according to claim 16 using an iterative procedure for determining the image of the subject and a step of the procedure uses an estimate up to the $n^{th}$ order scatter, n being equal to one or more, and a subsequent step uses an estimate up to a scatter of order higher than n.

18. A method according to claim 16 using an iterative procedure for determining the image of the subject, wherein elements used in the calculation of a scatter estimate for a step of the procedure are cached for reuse in a subsequent step.

19. A method according to claim 1, wherein the first scatter probability and the second scatter probability are dependent and are jointly calculated as a multiple scatter probability.

20. A computer program stored on a computer-readable storage device associated with a positron emission tomography scanner, the computer program comprising instruction operable to cause a computer to perform a method for calculating a scatter estimate for annihilation photons in a subject having a distribution of attenuation for scatter correction of detection data from a positron emission tomographic scanner, the method comprising the steps of:
   selecting a first scatter point $S_1$ and a second scatter point $S_2$ for the detection data for the subject from the positron emission tomographic scanner,
   determining a first scatter probability for scattering of a photon at scatter point $S_1$ and a second scatter probability for scattering of a photon at scatter point $S_2$,
   determining an integral of the attenuation over a line connecting $S_1$ and $S_2$,
   multiplying the integral and the scatter probabilities and using the product in the calculation of the scatter estimate.

* * * * *